United States Patent [19]

Andersson et al.

[11] Patent Number: 5,642,728
[45] Date of Patent: Jul. 1, 1997

[54] SYSTEM FOR DISPENSING PHARMACEUTICALLY ACTIVE COMPOUNDS

[75] Inventors: Jan Andersson, Södra Sandby; Hans Jägfeldt; Eva Trofast, both of Lund; Kjell Wetterlin, Södra Sandby, all of Sweden

[73] Assignee: AB Astra, Sodertalje, Sweden

[21] Appl. No.: 654,006

[22] Filed: May 29, 1996

Related U.S. Application Data

[63] Continuation of Ser. No. 165,402, Dec. 10, 1993, abandoned.

[30] Foreign Application Priority Data

Dec. 11, 1992 [SE] Sweden ................. 9203743

[51] Int. Cl.$^6$ ................................................ A61M 15/00
[52] U.S. Cl. ..................... 128/203.15; 128/203.12; 128/203.23
[58] Field of Search ............. 128/200.14, 200.23, 128/200.24, 203.12, 203.15, 203.23, 203.21, 202.21

[56] References Cited

U.S. PATENT DOCUMENTS

| 4,143,658 | 3/1979 | Rambosek et al. | 128/203.15 |
|---|---|---|---|
| 4,524,769 | 6/1985 | Wetterlin | 128/203.15 |
| 4,534,345 | 8/1985 | Wetterlin | 128/203.15 |
| 4,570,630 | 2/1986 | Elliott et al. | 128/203.15 |
| 4,627,432 | 12/1986 | Newell et al. | 128/203.15 |
| 4,667,668 | 5/1987 | Wetterlin | 128/203.15 |
| 4,668,218 | 5/1987 | Virtanen | 604/58 |
| 4,907,583 | 3/1990 | Wetterlin et al. | 128/203.15 |
| 4,973,582 | 11/1990 | Yoshida et al. | 514/78 |
| 5,161,524 | 11/1992 | Evans | 128/203.15 |
| 5,190,029 | 3/1993 | Byron et al. | 128/200.14 |
| 5,204,113 | 4/1993 | Hartley et al. | 424/45 |
| 5,327,883 | 7/1994 | Williams et al. | 128/203.12 |
| 5,341,800 | 8/1994 | Clark et al. | 128/203.15 |
| 5,349,947 | 9/1994 | Newhouse et al. | 128/203.21 |

FOREIGN PATENT DOCUMENTS

| 0069715 | 6/1982 | European Pat. Off. . |
|---|---|---|
| 0237507 | 2/1987 | European Pat. Off. . |
| 0530440 | 6/1992 | European Pat. Off. . |
| WO92/04069 | 3/1992 | WIPO . |
| WO93/17728 | 9/1993 | WIPO . |

OTHER PUBLICATIONS

Murray, John F. et al., "Textbook of Respiratory Medicine," vol. 1, 2d ed., pp.362–3 (W.B. Saunders Co., Phila., 1988, 1994).

Earle B. Weiss et al., Brochial Asthma: mechanisms and therapueitcs, Little, Brown & Co. (Boston: 1985, 1993), pp. 727–729.

Borgström, A Possible New Approach of Comparing Different Inhalers and Inhaled Substances, J. Aerosol. Med. 5:298, 1992.

(List continued on next page.)

*Primary Examiner*—Vincent Millin
*Assistant Examiner*—Eric P. Raciti
*Attorney, Agent, or Firm*—Fish & Richardson P.C.

[57] ABSTRACT

A method is provided for dispensing a clinically effective dose of an inhalable, pharmaceutically active compound. The method includes providing a dry powder inhaler containing a powder including the pharmaceutically active compound, and administering to a patient a dose of the compound that is less than 70% of the dose that would be necessary to obtain a physiologically equivalent result were the compound administered by a pressurized metered dose inhaler. The pharmaceutically active compound is in the form of primary particles at least 80% of which have a particle size of less than 10 microns, and the primary particles are provided as agglomerates which are deagglomerated during inhalation so that at least 40% of the dose administered is in the form of primary particles.

4 Claims, 2 Drawing Sheets

OTHER PUBLICATIONS

Thorsson et al., Lung Deposition of Budesonide from Turbuhaler is Twice that from a Pressurized Metered Dose Inhaler (pMDI), Poster presented at the British Thoracic Society Winter Meeting, London, UK, Dec. 9–11, 1992.

Bogaard et al., Dose–effect Relationship of Terbutaline Using a Multi–dose Powder Inhalation System ('Turbuhaler') . . . Powder Inhalation ('Rotahaler') in Asthmatics, Pharmatherapeutica 5:400–406, 1989.

Tukiainen and Terho, Comparison of Inhaled Salbutamol Powder and Aerosol in Asthmatic Patients with Low Peak Expiratory Flow Level, Eur. J. Clin. Pharamcol. 27:645–647, 1985.

Zainudin et al., Comparison of Bronchodilator Responses and Deposition Patterns of Salbutamol Inhaled from a Pressurised . . . Dose Inhaler, as a Dry Powder, and as a Nebulised Solution, Thorax 45:469–473, 1990.

PCT Search Report in the corresponding PCT Application No. 9203743–1.

SYSTEM FOR DISPENSING PHARMACEUTICALLY ACTIVE COMPOUNDS

This is a continuation of application Ser. No. 08/165,402, filed Dec. 10, 1993, now abandoned.

This invention relates to a dry powder inhaler system for dispensing a clinically effective dose of a pharmaceutically active compound.

BACKGROUND OF THE INVENTION

Inhalable drugs are commonly used in the treatment of diseases of the airways, such as rhinitis, asthma, and chronic bronchitis. Examples of such drugs include β2-adrenoreceptor agonists such as salbutamol, terbutaline, rimiterol, fenoterol, reproterol, adrenaline, pirbuterol, isoprenaline, orciprenaline, bitolterol, salmeterol, formoterol, clenbuterol, procaterol, broxaterol, picumeterol, TA-2005, mabuterol and the like, and their pharmacologically acceptable esters and salts; anticholinergic bronchodilators such as ipratropium bromide and the like; glucocorsticosteroids such as betamethasone, fluticasone, budesonide, tipredane, dexamethasone, betamethasone, flucinolone, triamcinolone, mometasone, D-5519 and the like, and their pharmacologically acceptable esters and salts; anti-allergy drugs such as sodium cromoglycate and nedocromil sodium; expectorants; antibiotics; mucolytics; antihistamines; cyclooxygenase inhibitors; leukotriene synthesis inhibitors; leukotriene antagonists, PLA2 inhibitors, PAF antagonists and prophylactics of asthma. In addition to these, some systemically active drugs might be deliverable via inhalation.

Inhalable drugs are commonly administered using either a metered dose inhaler (MDI) or a dry powder inhaler (DPI). The MDI, in which the drug is dissolved or suspended in a liquid propellant mixture (sometimes including small amounts of a volatile organic or inorganic solvent) stored in a pressurized container, is currently the more widely used device. In using an MDI, a patient activates the device to release a dose of the drug/propellant in coordination with inhalation through the mouth.

In a DPI, the drug is in the form of a dry powder, sans propellant. This type of device dispenses drug by means of the particle cloud generated by the airflow obtained upon patient inhalation through the mouth.

The aim of both the MDI and the DPI is to deposit a clinically effective amount of active compound in the lungs of the patient. By "clinically effective amount of active compound" is meant that amount of active compound which is required in order to effect the desired clinical response.

If handled correctly, MDI's and many DPI's deliver pharmaceuticals to the active site with approximately the same efficiency; however the amount of active substance which actually reaches the lungs in each case may be only approximately 10% of the amount in the metered dose. Therefore, in order to ensure that a clinically effective amount of active compound reaches the lungs, this metered dose must necessarily contain an amount of active compound many times greater than the clinically effective amount. The active compound which does not reach the lungs is lost mainly in the apparatus itself, and in the gastrointestinal tract. This is disadvantageous, since loss of active substance in the apparatus is costly and may reduce efficiency further, by for example clogging the mouthpiece or inhalation channel. More significantly for the patient, loss in the gastrointestinal tract can trigger or accentuate side effects associated with the use of any effective pharmaceutical. In the case of bronchodilators, for example, possible side effects commonly include tremor and increased heart rate, and irritation of the hyperreactive airways of many sufferers of airway disease.

It is known that optimal deposition of powder particles in the lung occurs when the particle diameter is under 10 microns, since particles having a diameter above this range are preferentially deposited in the mouth and throat. However, such fine powder will typically tend either to cling to the sides of its container, or to clump, so that a high proportion of the powder takes the form of large, loosely structured agglomerates of a size much larger than 10 microns, and only a small percentage of the powder particles remain within the primary particle diameter range. Certain new types of dry powder inhalers, including those described in European Patent Nos. 0 237 507 and 69 715 (e.g., the TURBUHALER®), are able to facilitate the delivery of a pharmaceutical powder in which a high proportion of the dispensed particles are of diameter in the desired range. This is accomplished by means of a mechanism or structural feature which causes the particle agglomerates to disintegrate during inhalation, yielding a significantly higher proportion of the powder in particles of the primary particle diameter range below 10 microns. It has generally been thought (see, for example, Bogaard et al. in "Pharmatherapeutica", Vol.5, No.6, 1989) that the efficiency of this new type of inhaler in delivering a clinically effective dose to the patient is comparable to the efficiency of previous dry powder inhalers (and therefore also to an MDI). Dosage levels recommended for a given pharmaceutical in the new type of inhaler have therefore been of the same order as those recommended for the same pharmaceutical in an MDI.

SUMMARY OF THE INVENTION

It has been found that administration of a pharmaceutically active compound by means of a dry powder inhaler device which delivers a large proportion of the powder in the form of particles having a diameter of less than 10 microns results in a markedly enhanced efficiency of delivery to the lungs, compared to delivery from standard pressurized metered dose inhalers (MDI's). This enhanced efficiency results from a decrease in the amount of the drug which is wasted due to adhesion to the interior of the device or to deposition in non-target areas, such as the mouth and throat of the patient, and is accompanied by a decrease in side effects attributable to such inappropriately deposited drug. Thus, the size of the nominal dose (also termed the metered dose) and the size of the dispensed dose used in the method of the invention can be substantially decreased visa vis the minimal corresponding dose required to achieve the same clinical effect as when an MDI is used by the same patient. By "nominal dose" or "metered dose" is meant the dose which is prepackaged in a single-dose inhaler, or which in a multidose inhaler is automatically measured out of a reservoir in preparation for inhalation. It thus represents the amount of compound measured before losses attributable to retention in the device, deposition in the mouth or throat, exhalation, etc. In contrast, "dispensed dose", as used herein, refers to the amount of compound which actually exits the inhaler. Devices useful in the method of the invention include the breath-actuated, dry powder inhalers described in EP 0 237 507, EP 69 715, WO 92/04069 and WO 93/17728, including the TURBUHALER® multidose inhaler and the MONOHALER® single-dose inhaler.

The invention thus includes a system for dispensing a clinically effective dose of a pharmaceutically active compound, which system includes a dry powder inhaler device containing a powder which includes the pharmaceutically active compound, wherein (a) of the metered dose of the compound in the inhaler (the "metered DPI dose"), at least 40% exits the inhaler in the form of powder particles less than about 10 microns in diameter;

(b) the metered DPI dose is sufficient to produce a clinically effective result in a patient; and (c) the amount of the compound in the metered DPI dose is not more than 70% (preferably not more than 50%) of the minimal amount of the compound which, when dispensed in a pressurized metered dose inhaler, produces an equivalent clinically effective result in the same patient (the "metered MDI dose"). Preferably, the amount of the compound which exits the inhaler of the invention upon dispensing of the metered DPI dose (the "dispensed DPI dose") is not more than 80% (preferably not more than 60%) of the amount of the same compound which exits the MDI upon dispensing of the metered MDI dose (the "dispensed MDI dose").

In order to dispense the pharmaceutically active compound in the form of particles of the necessary diameter, the powder contained in the inhaler is preferentially made up of primary particles or agglomerates of primary particles, which primary particles preferably are micronized particles at least 80% (and more preferably at least 90%) of which have a particle diameter of less than about 10 microns. More preferably, at least 50% (and even more preferably at least 60%) of the primary particles have a diameter of less than about 5 microns.

By processing the primary particles into sturdy agglomerates containing multiple primary particles each, the physical properties of the powder during storage, handling, and measuring are improved, and less powder is lost on the sidewalls of the device. The agglomerates remain friable, however, so that just prior to entering the respiratory track of the patient, they are readily pulverized into much smaller agglomerates and/or discrete primary particles of a diameter appropriate for deposition in the lung (i.e., less than 10 microns, and preferably less than 5 microns). In some types of DPI's (e.g., TURBUHALER and MONOHALER), this deagglomeration is accomplished by a design which creates air turbulence within the device from the air flow generated by inhalation through the device.

The pharmaceutically active compound of the present invention may, if desired, be contained in a pharmaceutical formulation containing commonly used additives such as diluents and/or carrier substances which are generally non-toxic, and chemically inert to the pharmaceutically active compound. For example a carbohydrate such as lactose, glucose, fructose, galactose, trehalose, sucrose, maltose, zylitol, myoinositol, dextrane, starch, or the like (or a hydrate thereof), and especially lactose, mannitol or myo-inositol; or an amino acid such as alanine, betaine, glycine, leucine, or the like, or any additive which will impart a desired property such as taste or a physiochemical or pharmaceutical property, may be employed. However, it is noted that the pharmaceutically active compound for use in the present invention requires no additives and may advantageously be used in its pure form. The powder, with or without additives, may be packaged in a capsule or loaded on an elongate carrying mechanism such as a tape, web or belt, wherein it is used in conjunction with an appropriate inhaler which dispenses the desired powder particles.

Any inhalable pharmaceutically active compound which can be formulated into a powder with the appropriate physiochemical, pharmaceutical and powder characteristics, as those characteristics are recognized in the art, is suitable for use in the present invention. Such characteristics include, for example, suitable particle size, agglomerability, deagglomerability, flowability, melting point, crystallinity and hygroscopicity. Examples of such pharmaceutically active compounds include drugs for the treatment of diseases of the airways, including $\beta$2-adrenoreceptor agonists such as salbutamol, terbutaline, rimiterol, fenoterol, reproterol, adrenaline, pirbuterol, isoprenaline, orciprenaline, bitolterol, salmeterol, formoterol, clenbuterol, procaterol, broxaterol, picumeterol, TA-2005, mabuterol and the like, and their pharmacologically acceptable esters and salts; anticholinergic bronchodilators such as ipratropium bromide and the like; glucocorsticosteroids such as betamethasone, fluticasone, budesonide, tipredane, dexamethasone, betamethasone, fluocinolone, triamcinolone, mometasone, D-5519 and the like, and their pharmacologically acceptable esters and salts; anti-allergic drugs such as sodium cromoglycate and nedocromil sodium; expectorants; mucolytics; antihistamines; cyclooxygenase inhibitors; leukotriene synthesis inhibitors; leukotriene antagonists, PLA2 inhibitors, PAF antagonists, and prophylactics of asthma. Alternatively, the pharmaceutically active compound could be any one of several types of inhalable, systemically active drugs, including antiarrhythmio drugs, tranquilizers, cardiac glycosides, hormones, antihypertensive drugs, antihypotensive drugs, antidiabetic drugs, antiparasitic drugs, anticancer drugs, sedatives and analgesic drugs, antibiotics, antirheumatic drugs, immunotherapeutics, antifungal drugs, vaccines, antiviral drugs, proteins, peptides, vitamins, cell surface receptor blockers, and others.

The present invention is especially useful when the pharmaceutically active compound is a $\beta$-2 agonist such as terbutaline, salbutamol, formoterol, budesonide or their salts or hydrates, or a mixture of any of such $\beta$-2 agonists (or their salts or hydrates) with a carbohydrate, especially lactose, mannitol or myoinositol. Examples include the following mixtures: ipratropium bromide plus lactose, formoterol plus budesonide, ipratropium bromide plus budesonide, terbutaline plus sodium cromoglycate, and terbutaline plus budesonide.

The metered DPI dose of a drug (delivered in accordance with the invention) can be directly compared to the metered MDI dose of the same drug, by reference to the published metered MDI dose of that drug (see, e.g., the Physicians' Desk Reference, published by Medical Economics Data, Montvale, N.J.). Generally the published metered MDI dose can be assumed to be the minimal metered MDI dose that is clinically effective. Alternatively, one of ordinary skill can prepare the drug in both MDI form and in accordance with the system of the invention, and determine, for comparative purposes, the minimal clinically effective metered dose and dispensed dose corresponding to each method. Yet another method would permit comparison of (1) the published metered MDI dose of one drug which targets a given medical condition, with (2) the metered DPI dose (delivered in accordance with the invention) of a second drug which targets the same medical condition. Since drugs targeted at the same disease are commonly not equipotent, even if they act by generally the same mechanism, the metered dose, dispensed dose, and of course the clinically effective amount of active compound will be different for these different drugs. For example, the $\beta$-2 agonist salbutamol is generally accepted as being more potent than the $\beta$-2 agonist terbutaline sulphate, 0.1 mg of salbutamol generally being regarded as equipotent to 0.25 mg of terbutaline sulphate. Therefore, in any assessment of efficiency comparing different drugs, equipotent doses of pharmaceutically active compounds should be directly compared. As disclosed herein, these recommended doses can be reduced when the system of the invention, rather than an MDI, is used to dispense the drugs. For example, the metered dose of each of salbutamol, budesonide and terbutaline may be reduced by a factor of two, compared to the metered dose dispensed from an MDI for an equivalent clinically therapeutic effect, in accordance with the present invention.

Also within the invention is a method for dispensing a clinically effective dose of a pharmaceutically active compound, which method includes the steps of identifying a patient in need of the compound (i.e., a patient suffering from a medical condition treatable with the compound), and causing the patient to inhale the compound from the dry powder inhaler system of the invention, as described above. Preferably, the patient is an adult, and the metered DPI dosage is no more than 70% of the metered MDI dosage appropriate for an adult of the same body weight. Alternatively, the patient is a child, and the metered DPI dosage is no more than 70% of the metered MDI dosage appropriate for a child of the same body weight. This method is thus useful for the treatment of a medical condition which is treatable with the pharmaceutically active compound in inhalable form.

Other features and advantages of the invention will be apparent from the following detailed description, and from the claims.

DETAILED DESCRIPTION

The invention will now be illustrated by Examples which are intended to illustrate but not limit the scope of the invention.

EXAMPLE 1: Particle size distribution

Figure 1:
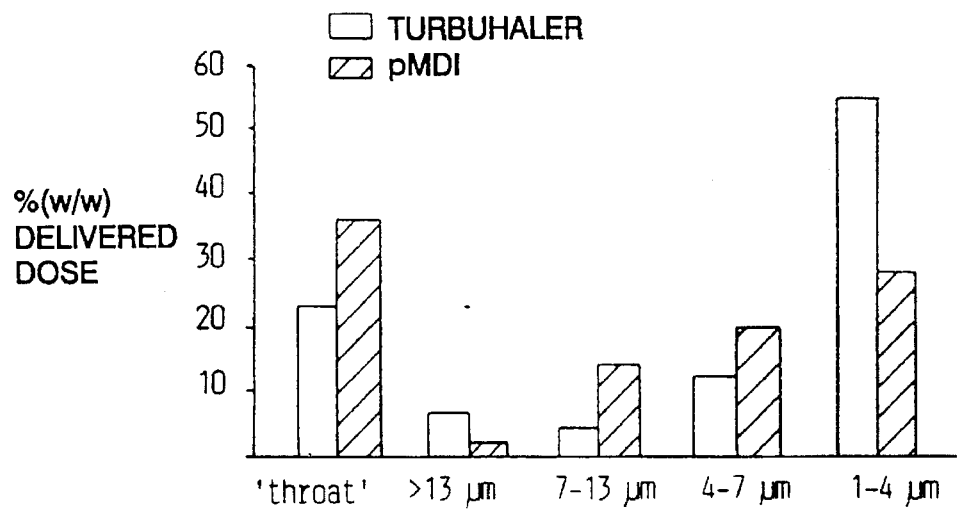
FIG. 1 is a bar graph comparing the particle size distribution of particles exiting a TURBUHALER inhaler and a MDI.

In vitro studies have shown that the delivery of powdered budesonide by the TURBUHALER inhaler at inspiratory flows of 60 liters/minute leads to a greater proportion of fine particles than does delivery by an MDI (PULMICORT™ budesonide MDI, AB Astra, Sweden). The measurements were performed with a four-stage (>13, 7–13, 4–7, and 1–4 microns) cascade impactor, which operates at a flow rate of 60 liters/minute. Five units of each device were separately tested. The results, presented in FIG. 1, illustrate that, under the conditions tested, more than half of the particles delivered by the TURBUHALER device made it to the stage corresponding to a diameter of 1 to 4 microns, and about two-thirds registered 7 microns or less.

EXAMPLE 2: TURBUHALER v. MDI
(Budesonide)

In order to determine the absolute systemic availability and the amount of budesonide deposited and absorbed in the lung after inhalation via TURBUHALER and via an MDI, 24 healthy subjects were given budesonide 1 mg as five inhalations of 200 micrograms each, via TURBUHALER inhaler or via MDI, and 0.5 mg intravenously, on separate study days. Budesonide levels were determined in plasma by a LC-MS method. The amount of budesonide absorbed in the lung was calculated on the assumption of an availability of swallowed budesonide of 13%. Furthermore, absorption in the lung was calculated in 13 of the subjects after inhalation with concomitant oral dosing of charcoal to prevent absorption of budesonide from the gastrointestinal track. There was good conformity between the two modes of calculation.

From TURBUHALER, the geometric mean of the absolute systemic availability of budesonide was 38%. For the MDI, this figure was 28%. CMAX and TMAX were 3.6 nmol/l and 0.3 hours with TURBUHALER, and 2.3 nmol/l and 0.5 hours with the MDI. The geometric mean of the amount of budesonide deposited and absorbed in the lung was 32% (16%–59%) for TURBUHALER and 15% (3%–47%) for the MDI. This shows a lung deposition of budesonide from TURBUHALER which is twice that from an MDI, and less variable, demonstrating that a lower metered dosage may be used when TURBUHALER is employed.

EXAMPLE 3: TURBUHALER v. MDI
(Terbutaline)

Eight healthy volunteers were administered terbutaline sulphate tagged with (99 m)Tc, using a TURBUHALER inhaler or a MDI on two separate days at least 48 hours apart in randomized cross-over fashion. In order to deposit approximately 10 MBq (99 m)Tc in the body on each study day, four doses of terbutaline sulphate (total 1 mg) were given by MDI and two doses of terbutaline sulphate (total 1 mg) were given by TURBUHALER. Administration of radioactive aerosol was performed with the inhaler connected in series with a Vitalograph MDI-compact spirometer (Vitalograph Ltd., UK) modified for measuring inhalation flows. The target average inhalation flow rate for the MDI trials was 30 l/min, and the target peak inhalation flow rate for the TURBUHALER inhaler trials was 60 l/min. These flow rates are believed to optimize drug delivery to the lungs for the two respective devices. After inhalation, the volunteers were instructed to hold their breath for 10 seconds before exhaling through an exhalation filter (Pall Ultipor, UK) that retains terbutaline inhaled into, but not deposited in, the lungs. The MDI was actuated by an investigator during the course of inhalation. Lung function tests were performed before and after inhalation of the labelled terbutaline to ensure that no deterioration in lung function had occurred. Immediately after inhalation of a study drug, posterior and anterior views of the lungs and a lateral view of the oropharynx were taken by gamma camera (General Electric Maxicamera) connected on line to a Nodecrest computer system. Gamma radiation from the mouthpiece and exhalation filter was also measured. All images were stored on magnetic tape for subsequent data analysis. From these measurements the fraction of the metered dose into the lungs could be determined. The measurements, when adjusted to take account of an observed mismatch between the distributions of unlabelled drug, labelled drug and radiolabel for the TURBUHALER inhaler, gave a mean value of 29.3% for total lung deposition (TURBUHALER), compared with 16.7% for a MDI. These figures indicate the feasibility of using a lower metered dose when TURBUHALER is employed rather than a MDI.

EXAMPLE 4: TURBUHALER v. MDI (Salbutamol)

Figure 2:
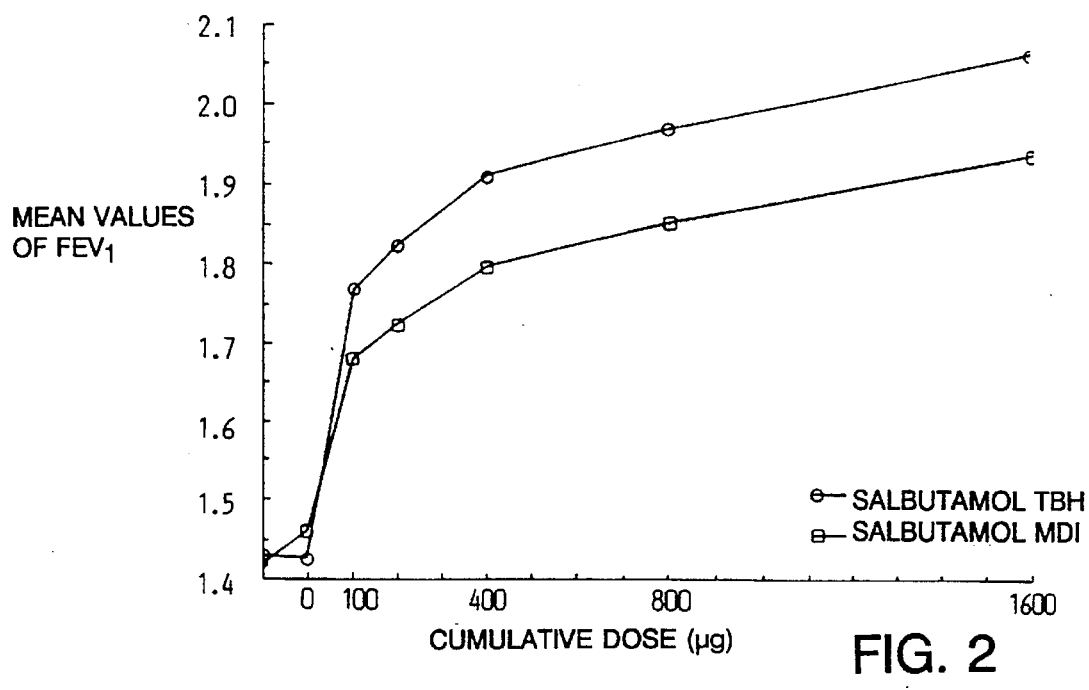
FIG. 2 is a graph comparing the clinical effect of various cumulative metered doses of salbutamol inhaled from a dry powder inhaler system of the invention, with the clinical effect of the same cumulative metered doses inhaled from a MDI. Clinical effect is expressed as mean values of forced expiratory volume in one second, $FEV_1(L)$, before dosing.
Figure 3:
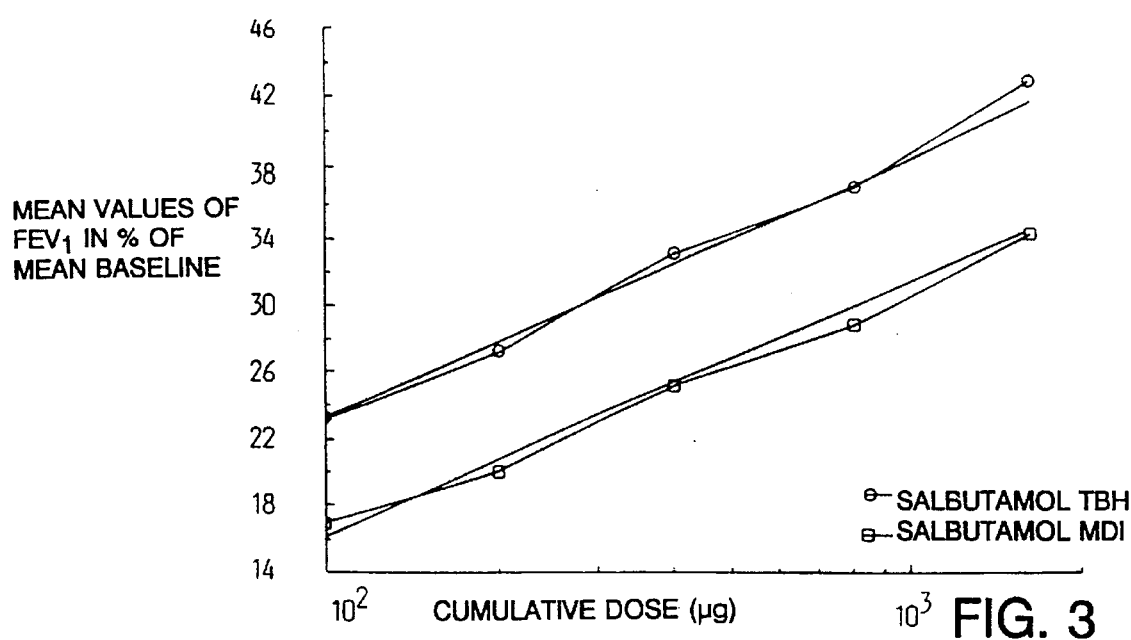
FIG. 3 is a graph comparing the mean values of $FEV_1(L)$ in percent of mean baseline, representing clinical effect, in patients given various cumulative metered doses of salbutamol via a MDI or a dry powder inhaler system of the invention.

The relative efficacy of cumulative doses (100 micrograms up to 1600 micrograms) of salbutamol in TURBUHALER and salbutamol in a MDI (Ventolin, Glaxo) was compared in 12 patients with reversible obstructive airway disease. The results, shown in FIGS. 2 and 3, indicate that salbutamol delivery is more efficient from the TURBUHALER inhaler than from the commercially marketed MDI. Therefore, the metered dose of salbutamol in a TURBUHALER system can be lower than the MDI metered dose, for the same clinical effect.

EXAMPLE 5: Particle Distribution (Salbutamol)

Figure 4:
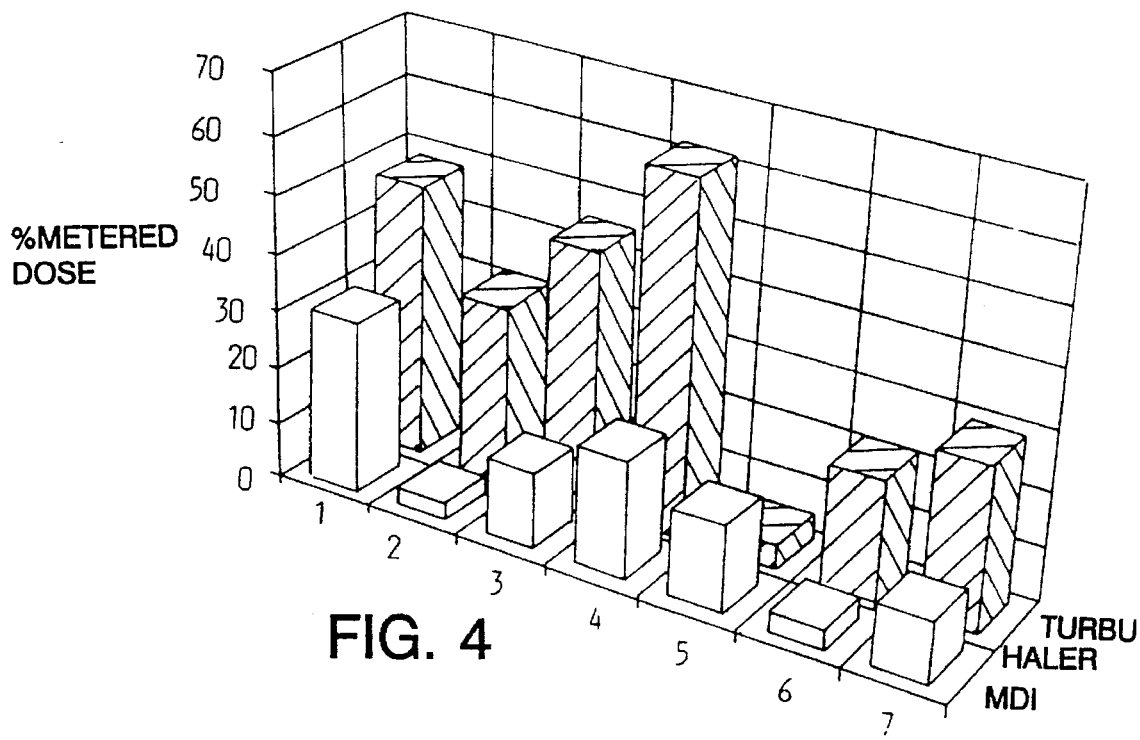
FIG. 4 is a bar graph comparing lung deposition of salbutamol inhaled via a pressurized MDI at the flow rate of 30–60 L/min, or via a dry powder inhaler system of the invention, at a mean peak inspiratory flow of 64 L/min, by healthy volunteers.

The absolute pulmonary deposition of salbutamol inhaled via TURBUHALER and a MDI was investigated. Salbutamol was mixed with lactose in order to achieve lower dosing without affecting the dosing accuracy. Individual data from 7 healthy volunteers indicated a difference in deposition favoring TURBUHALER. The results are presented in FIG. 4.

EXAMPLE 6: MONOHALER (Budesonide)

Particle size distribution from the MONOHALER single dose inhaler has been found to be comparable with that of the TURBUHALER multidose inhaler (data not shown). This indicates that this single-dose inhaler also is appropriate for use in the system and methods of the invention, and an efficiency of delivery comparable to that of the TURBUHALER can be expected.

Other embodiments are within the following claims.
What is claimed is:

1. A method for dispensing a dose of a pharmaceutically active compound selected from the group consisting of salbutamol and a salt, hydrate or ester of salbutamol, which method comprises
    (1) identifying a patient in need of treatment with said compound;
    (2) providing a breath-actuated, dry powder inhaler device containing a powder comprising said compound, wherein
        (a) said powder stored within said device consists essentially of agglomerates of primary particles, at least 80% of said primary particles having a diameter of less than about 10 microns,
        (b) said device comprises a metered dose of said compound sufficient to produce a predetermined clinically predetermined effective result in said patient, said metered dose containing an amount of said compound less than or equal to 70% by weight of the amount of said compound which would be required to produce said predetermined equivalent clinically effective result were the compound administered by a standard pressurized metered dose inhaler; and
        (c) said device comprises a means for using air turbulence to obtain substantial deagglomeration of the primary particles prior to their exiting said device, so that of said metered dose, at least 40% exits said device in the form of unagglomerated particles less than about 10 microns in diameter, and
    (3) administering said metered dose to the patient by causing the patient to inhale through said device, thereby creating sufficient air turbulence in said device to cause said metered dose of agglomerated primary particles to be substantially deagglomerated prior to exiting said device, such that at least 40% of said metered dose exits said device in the form of unagglomerated particles less than about 10 microns in diameter.

2. The method of claim 1, wherein said inhaler device is a multidose, breath-activated inhaler.

3. The method of claim 1, wherein said powder additionally comprises a carbohydrate.

4. The method of claim 1, wherein said powder additionally comprises an amino acid.

* * * * *